US008309714B2

(12) United States Patent
Kugimoto et al.

(10) Patent No.: US 8,309,714 B2
(45) Date of Patent: *Nov. 13, 2012

(54) PROCESS FOR PRODUCING LAUROLACTAM

(75) Inventors: Junichi Kugimoto, Ube (JP); Joji Kawai, Ube (JP); Hideo Shimomura, Ube (JP); Ryouta Yasumatsu, Ube (JP); Nobuhiro Ii, Ube (JP)

(73) Assignee: Ube Industries, Ltd., Ube-shi (JP)

(*) Notice: Subject to any disclaimer, the term of this patent is extended or adjusted under 35 U.S.C. 154(b) by 200 days.

This patent is subject to a terminal disclaimer.

(21) Appl. No.: 12/744,675

(22) PCT Filed: Nov. 19, 2008

(86) PCT No.: PCT/JP2008/071044
§ 371 (c)(1), (2), (4) Date: May 25, 2010

(87) PCT Pub. No.: WO2009/069522
PCT Pub. Date: Jun. 4, 2009

(65) Prior Publication Data
US 2010/0267944 A1 Oct. 21, 2010

(30) Foreign Application Priority Data

Nov. 29, 2007 (JP) ................. 2007-308746

(51) Int. Cl.
C07D 201/04 (2006.01)
C07D 225/02 (2006.01)
(52) U.S. Cl. ..................................... 540/464
(58) Field of Classification Search .............. 540/464
See application file for complete search history.

(56) References Cited

U.S. PATENT DOCUMENTS

| 3,410,832 A | 11/1968 | Griehl et al. |
| 3,431,255 A | 3/1969 | Strauss et al. |
| 3,437,655 A | 4/1969 | Garritsen et al. |
| 3,462,417 A | 8/1969 | Simmrock et al. |
| 6,649,757 B2 | 11/2003 | Kuroda et al. |
| 2002/0058840 A1 | 5/2002 | Thiele et al. |
| 2003/0065220 A1 | 4/2003 | Schiffer et al. |
| 2003/0139596 A1 | 7/2003 | Kuroda et al. |

FOREIGN PATENT DOCUMENTS

| EP | 487090 A | 5/1992 |
| EP | 2123635 A1 | 11/2009 |
| GB | 1148013 | 4/1969 |
| JP | 43-12153 B1 | 5/1943 |
| JP | S46-023740 B | 7/1971 |
| JP | S47-018114 B | 5/1972 |
| JP | S52-033118 B | 8/1977 |
| JP | H05-004964 A | 1/1993 |
| JP | H09-301951 A | 11/1997 |
| JP | H09-301952 A | 11/1997 |
| JP | 2001-019670 A | 1/2001 |
| JP | 2001-072658 A | 3/2001 |
| JP | 2001-302602 A | 10/2001 |
| JP | 2001-302603 A | 10/2001 |
| JP | A-2002-114746 | 4/2002 |
| JP | 2003-081930 A | 3/2003 |
| JP | 2003-321453 A | 11/2003 |
| JP | A-2004-099585 | 4/2004 |
| JP | 2006-219470 A | 8/2006 |
| WO | WO 2007/105482 A1 | 9/2007 |
| WO | WO 2007/125002 A1 | 11/2007 |
| WO | WO 2008/096873 A1 | 8/2008 |

OTHER PUBLICATIONS

Furuya, Y. et al., Journal of American Chemical Society, pp. 11240-11241. (2005).
Narasaka et al., Chemistry Letter, pp. 489-492 (1993).
Sandhu et al., Indian Journal of Chemistry, pp. 154-156 (2002).
Yadav et al., Journal of Chemical Research(S), pp. 236-238 (2002).
Ishihara et al., Journal of American Chemical Society pp. 11240-11241 (2005).
Zhu et al., Tetrahedron Letters, pp. 4861-4863 (2006).
International Search report issued in corresponding PCT Application No. PCT/JP2008/071044 mailed Feb. 24, 2009.
International Preliminary Report on Patentability and Written Opinion corresponding to PCT Application No. PCT/JP2008/071044, issued Jun. 8, 2010.
English translation of the International Preliminary Report on Patentability of PCT/JP2008/052192.
Supplementary European Search Report in corresponding EP Application No. 08853278.3, dated Sep. 26, 2011.

*Primary Examiner* — Bruck Kifle
(74) *Attorney, Agent, or Firm* — Knobbe Martens Olson & Bear LLP

(57) ABSTRACT

Provided is a process for efficiently producing laurolactam by simple steps from cyclododecanone and hydroxylamine. This production process comprises the steps of: (a) reacting cyclododecanone with hydroxylamine in an aqueous solution in the presence of an oxime-formation solvent to produce cyclododecanone oxime; (b) separating the reaction mixture obtained after the oxime-forming step into an oil and an aqueous phases and collecting a solution of cyclododecanone oxime of the oil phase; (c) removing a part or all of the oxime-formation solvent and dissolved water from the solution of cyclododecanone oxime which is collected as an oil phase in the oil/aqueous phase separation step, whereby preparing a solution containing a rearrangement solvent to be used in a rearrangement reaction in a later step and the cyclododecanone oxime; (d) producing laurolactam from cyclododecanone oxime by rearrangement reaction using an aromatic-ring containing compound as a rearrangement catalyst; and (e) separating and removing the rearrangement solvent and the rearrangement catalyst from the reaction mixture after the rearrangement step, and purifying the laurolactam.

7 Claims, 2 Drawing Sheets

US 8,309,714 B2

PROCESS FOR PRODUCING LAUROLACTAM

This application is the U.S. National Phase under 35 U.S.C. §371 of International Application PCT/JP2008/071044, filed Nov. 19, 2008 designating the U.S., and published in Japanese as WO2009/069522 on Jun. 4, 2009, which claims priority to Japanese Patent Application No. 2007-308746, filed Nov. 29, 2007.

TECHNICAL FIELD

The present invention relates to a process for producing laurolactam from cyclododecanone and hydroxylamine by an industrially convenient process.

BACKGROUND ART

A common industrial process for producing an amide compound involves Beckmann rearrangement of a corresponding oxime compound. For example, ε-caprolactam which is industrially useful is produced by Beckmann rearrangement of cyclohexanone oxime. Rearrangement catalysts used are generally concentrated sulfuric acid and oleum. Since these strong acids must be used in the stoichiometric amounts or more, they form a large amount of ammonium sulfate as a byproduct during neutralization. Although laurolactam, which is a starting material for Nylon 12, is also produced in a similar manner, the process is more complex because cyclododecanone oxime as an intermediate product has a high melting point. In producing ε-caprolactam, both cyclohexanone oxime and ε-caprolactam have a relatively lower melting point, so that oxime formation or rearrangement can be conducted in a solvent-free system, but production of laurolactam requires a reaction solvent. This reaction solvent must be able to substantially dissolve cyclododecanone oxime and be inert to concentrated sulfuric acid or oleum, and therefore the selection of the solvent is considerably restricted.

Only two processes are known for industrially producing laurolactam from cyclododecanone and an aqueous solution of hydroxylamine. One is a process commercially developed by Degussa Company. This method is as follows. Cyclododecanone is converted into an oxime using isopropylcyclohexane as a solvent, and after separating layers, a resulting solution of cyclododecanone oxime in isopropylcyclohexane is slowly added to concentrated sulfuric acid at a low temperature to prepare a solution of a cyclododecanone oxime sulfate adduct in sulfuric acid. After separating and recovering isopropylcyclohexane, the residual solution of cyclododecanone oxime sulfate adduct in sulfuric acid is heated to initiate Beckmann rearrangement of the oxime. After the rearrangement reaction, water is added to the system to dilute sulfuric acid, and then, the laurolactam produced is extracted with an organic solvent. Here, the extraction solvent may be isopropylcyclohexane or cyclododecanone. The extraction solvent is recovered by distillation from the resulting extraction solution and then laurolactam in the residue is purified by distillation (see, Patent Reference No. 1).

This process does not generate ammonium sulfate as a byproduct in the rearrangement reaction step, but requires enormously large facilities and energy for treating a large amount of waste diluted sulfuric acid. Furthermore, since cyclododecanone reacts with concentrated sulfuric acid to form a byproduct, the oxime-forming reaction must be completed for eliminating residual cyclododecanone, but due to hydrophobicity of isopropylcyclohexane, a mass transfer rate is low in an oil-water interface, leading to a longer oxime-forming reaction. As a whole, the process involves many steps of separation, recovery and recycling of solvents and, therefore, requires considerably large equipment expenses and energy.

Another industrial process is that commercially developed by Ube Industries-EMS. This process utilizes the fact that cyclohexanone oxime and caprolactam are good solvents for cyclododecanone oxime and laurolactam, respectively (for example, see Patent Reference 2). Specifically, a mixture of cyclododecanone and cyclohexanone is blended with an aqueous solution of hydroxylamine to produce oximes. Cyclohexanone oxime produced has a low melting point and is a good solvent for cyclododecanone oxime, so that the reaction can be conducted at 100° C. or lower and at an ambient pressure. Furthermore, cyclohexanone oxime is adequately hydrophilic for the oxime-forming reaction to quickly proceed, and the mixture is transferred to the rearrangement step without residual cyclohexanone or cyclododecanone. A rearrangement catalyst used is concentrated sulfuric acid or oleum. Whereas laurolactam produced has a high melting point, it is highly soluble in caprolactam having a low melting point. Therefore, the reaction can be carried out even at a temperature of 100° C. or lower. The resulting rearrangement reaction solution is neutralized with ammonia water and then extracted with an organic solvent. Caprolactam can be dissolved in water to some extent, but is extracted into an organic solvent due to salting-out effect of ammonium sulfate. Next, a large amount of water is added to the solution containing extracted laurolactam and caprolactam, and caprolactam is extracted into the aqueous phase. From the separated organic phase, the organic solvent is recovered and laurolactam is purified by distillation. The aqueous phase is concentrated and after removing impurities, caprolactam is purified.

This process is excellent in that laurolactam and caprolactam can be produced together. However, as a process for producing laurolactam, it has the following problems; (1) separation and purification of caprolactam requires large amounts of equipment expenses, resulting in low investment efficiency and the process involves operations of low energy efficiency such as concentration of an aqueous solution of caprolactam; (2) there is a restriction to a production ratio of laurolactam/caprolactam; and (3) caprolactam is a low-value-added product in comparison with laurolactam and an use efficiency of hydroxylamine is low.

Recently, there have been intensely investigated rearrangement catalysts which do not require a large amount of sulfuric acid or oleum. As a system containing a strong acid, there have been reported a mixture of rhenium peroxide ammonium salt and trifluoromethane sulfonic acid (Non-Patent Reference 1), indium triflate (Non-Patent Reference 2) and ytterbium triflate (Non-Patent Reference 3). Known methods utilizing a system containing an acid and a dehydrating agent include a method of conducting rearrangement reaction using phosphorous pentoxide or a condensed phosphoric acid compound and a fluorine-free sulfonic anhydride or sulfocarboxylic anhydride in a N,N-disubstituted amide compound as a solvent (Patent References 3 and 4) and a method using a zeolite catalyst pre-treated with an aqueous acid-containing solution (Patent Reference 5). As methods that use no acids, there have been suggested a method of conducting rearrangement reaction in the presence of a rhenium compound and a nitrogen-containing heterocyclic compound (Patent References 6 and 7) and a method of using zinc oxide (Patent Reference 8). Patent Reference 9 has disclosed a method of reacting an oxime and a carboxylic acid in a carboxylic acid solvent using cyanuric chloride (trichlorotriazine) as a dehydrating agent, whereby producing an ester which is then subjected to rearrangement reaction. Patent Reference 10 has disclosed a method where an oxime hydrochloride is subjected to rearrangement using cyanuric chloride (trichlorotriazine) as an initiator.

Although some of these catalysts and manufacturing processes can provide a high rearrangement yield, these methods employ special catalysts and/or solvents, for which a recovering or recycling procedure is not disclosed, and these are, therefore, unestablished as an industrial process.

Patent Reference 11 has described Beckmann rearrangement of an oxime compound in a polar solvent, wherein a rearrangement catalyst used is an aromatic compound (1) containing, as aromatic-ring member, at least one carbon atom having a leaving group, (2) containing at least three aromatic-ring members which are either or both of heteroatoms or/and carbon atoms having an electron-withdrawing group, and (3) wherein, two of the heteroatoms and/or carbon atoms having an electron-withdrawing group are at the ortho- or para-position to the carbon atom having an electron-withdrawing group. A similar description can be found in Non-Patent Reference 4. Non-Patent Reference 5 discloses that a phosphoric acid salt having a heterocyclic structure similar to that in Patent Reference 11 is active for Beckmann rearrangement.

The catalyst disclosed in Patent Reference No. 11 is highly active for a rearrangement reaction of cyclododecanone oxime to provide laurolactam in a high yield, and is, therefore, suitable as a rearrangement reaction catalyst in producing laurolactam. However, the solvents used in the rearrangement reaction are polar solvents, specifically, a nitrile which is recommended as a solvent cannot be used for an oxime-forming reaction because it reacts with hydroxylamine to form an amidoxime. Furthermore, since it is susceptible to hydrolysis, the loss of the catalyst inevitably happens in the step of removing catalyst and the like. Since it is highly miscible with water, a process for dehydrating materials for rearrangement becomes complex. Therefore, for establishing a practically feasible industrial process, solvents and processes must be selected, in consideration of individual steps from starting materials to a final product including an oxime-forming step.

Patent Reference 1: Japanese examined patent publication No. S52-033118 (1977-033118).
Patent Reference 2: Japanese Laid-open patent publication No. H05-4964 (1993-4964).
Patent Reference 3: Japanese Laid-open patent publication No. 2001-302602.
Patent Reference 4: Japanese Laid-open patent publication No. 2001-302603.
Patent Reference 5: Japanese Laid-open patent publication No. 2001-072658.
Patent Reference 6: Japanese Laid-open patent publication No. H09-301951 (1997-301951).
Patent Reference 7: Japanese Laid-open patent publication No. H09-301952 (1997-301952).
Patent Reference 8: Japanese Laid-open patent publication No. 2001-019670.
Patent Reference 9: Japanese examined patent publication No. S46-23740 (1971-23740).
Patent Reference No. 10: Japanese examined patent publication No. S47-18114 (1972-18114).
Patent Reference No. 11: Japanese Laid-open patent publication No. 2006-219470.
Non-Patent Reference 1: K. Narasaka, et. al., Chemistry Letter, pp. 489-492 (1993).
Non-Patent Reference 2: J. S. Sandhu, et. al., Indian Journal of Chemistry, pp. 154-156 (2002).
Non-Patent Reference 3: J. S. Yadav, et. al., Journal of Chemical Research(S), pp. 236-238 (2002).
Non-Patent Reference 4: K. Ishihara, et. al., Journal of American Chemical Sociaty, pp. 11240-11241 (2005).
Non-Patent Reference 5: M. Zhu, et. al., Tetrahedron Letters, pp. 4861-4863 (2006).

DISCLOSURE OF THE INVENTION

Subject to be Solved by the Invention

An objective of the present invention is to provide a process for efficiently producing laurolactam from cyclododecanone and hydroxylamine by a convenient process. Another objective of the present invention is to provide a process for producing laurolactam using a combination of inexpensive facilities.

Means to Solve the Subject

The present invention relates to the following items.
1. A process for producing laurolactam comprising the steps of:
    (a) reacting cyclododecanone with hydroxylamine in an aqueous solution in the presence of an organic solvent (hereinafter, referred to as "oxime-formation solvent") to produce cyclododecanone oxime (hereinafter, referred to as an "oxime-forming step");
    (b) separating the reaction mixture obtained after the oxime-forming step into an oil and an aqueous phases and collecting a solution of cyclododecanone oxime of the oil phase (hereinafter, referred to as an "oil/aqueous phase separation step");
    (c) removing a part or all of the oxime-formation solvent and dissolved water from the solution of cyclododecanone oxime which is collected as an oil phase in the oil/aqueous phase separation step, whereby preparing a solution containing a solvent to be used in a rearrangement reaction in a later step (hereinafter, referred to as "rearrangement solvent") and the cyclododecanone oxime (hereinafter, referred to as a "dehydration/solvent preparation step");
    (d) producing laurolactam from cyclododecanone oxime by rearrangement reaction using an aromatic-ring containing compound as a rearrangement catalyst (hereinafter, referred to as a "rearrangement step"); and
    (e) separating and removing the rearrangement solvent and the rearrangement catalyst from the reaction mixture obtained after the rearrangement step, and purifying the laurolactam (hereinafter, referred to as a "separation/purification step").
2. The process for producing laurolactam according to the above item 1, wherein the organic compound used for the rearrangement catalyst is an aromatic-ring containing compound; the aromatic ring having a structure (1) comprising at least one carbon atom having a leaving group as a ring member of the aromatic ring and (2) comprising at least two carbon atoms having an electron-withdrawing group as ring members of the aromatic ring, and (3) wherein, three of the nitrogen atoms and/or the carbon atoms having an electron-withdrawing group, each of which is a ring member of the aromatic ring, are at the ortho and the para positions to the carbon atom having a leaving group described in (1).
3. The process for producing laurolactam according to the above item 2, wherein the aromatic ring is benzene, pyridine, pyrimidine or triazine and comprises a halogen atom as the leaving group.

4. The process for producing laurolactam according to the above item 2, wherein the organic compound used for the rearrangement catalyst is selected from the group consisting of 4-chloro-3,5-dinitrobenzonitrile, picryl chloride, 2-chloro-3,5-dinitropyridine and trichlorotriazine.

5. The process for producing laurolactam according to any one of the above items 1 to 4, wherein in the dehydration/solvent preparation step, a content of residual water in the cyclododecanone oxime solution to be fed to the rearrangement step is reduced to 1000 ppm or less.

6. The process for producing laurolactam according to the above item 5, wherein in the dehydration/solvent preparation step, a content of residual water in the cyclododecanone oxime solution to be fed to the rearrangement step is reduced to 100 ppm or less.

7. The process for producing laurolactam according to any one of the above items 1 to 6, wherein the rearrangement solvent is a nonpolar solvent.

8. The process for producing laurolactam according to the above item 7, wherein the rearrangement solvent is one or more solvents selected from the group consisting of alicyclic hydrocarbon, aromatic hydrocarbon and fused-aromatic-ring hydrogenated-product.

9. The process for producing laurolactam according to the above item 7 or 8, wherein prior to the oil/aqueous phase separation step, the rearrangement solvent is added and the oxime-formation solvent is removed by distillation in the dehydration/solvent preparation step.

10. The process for producing laurolactam according to the above item 7 or 8, wherein the oxime-formation solvent and the rearrangement solvent are an identical organic solvent, and a portion thereof is removed by distillation in the dehydration/solvent preparation step.

Effect of the Invention

Since the present invention does not employ concentrated sulfuric acid or oleum, byproducts such as ammonium sulfate are not produced, and the required steps such as neutralization, extraction/separation and distillation/collection are significantly reduced in comparison with the conventional methods and therefore a convenient process for producing laurolactam is realized.

Since solvents suitable for each reaction are also selected as the oxime-formation solvent and rearrangement solvent, the oxime-formation and rearrangement reaction can be completed in a short time, and laurolactam can be obtained in a high yield.

Since furthermore nonpolar organic solvent stable thermally and chemically is employed for the rearrangement solvent in a preferred embodiment of the present invention, the solvent can be readily collected in a high yield and recycled.

DETAILED DESCRIPTION OF THE INVENTION

Figure 1:
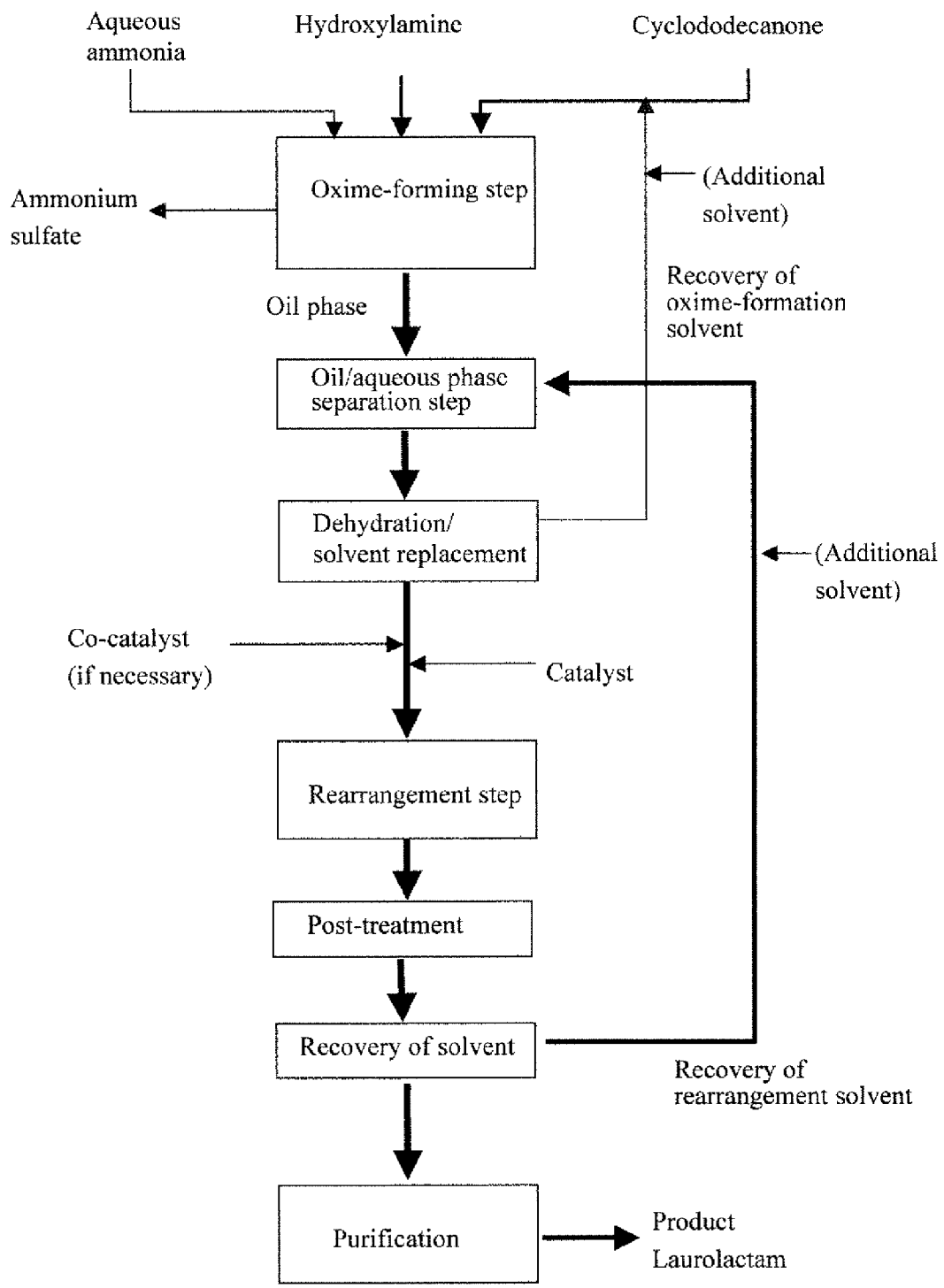
FIG. 1 is a flowchart showing the process flows of Examples 1 to 4.

Hereafter, the present invention will be explained in detail. In the process for producing laurolactam, it is of vital importance to select the rearrangement catalyst and rearrangement solvent. In the present invention, in addition to that an efficient reaction system is selected, the total optimization as an industrial process is further considered. Hereafter, each step will be explained.

The oxime-forming step is a step to produce cyclododecanone oxime by reacting cyclododecanone with hydroxylamine aqueous solution in an equivalent mole.

Cyclododecanone used for a stating material can be readily available as an industrial agent. For example, Invista Company sells a mixture of cyclododecanone and cyclododecanol, and therefore, after cyclododecanol in the mixture is converted by dehydrogenation into cyclododecanone, the product can be used.

The other starting material, hydroxylamine, which is unstable, is produced and sold as an aqueous solution of a hydroxylamine salt such as hydroxylamine sulfate and hydroxylamine carbonate. Before the reaction, a base such as ammonia water is added to the solution to liberate hydroxylamine, which is to be used. An aqueous solution of hydroxylamine in which hydroxylamine has been already liberated may be fed to the oxime-forming step, but generally, an aqueous solution of a hydroxylamine salt (preferably, sulfate) and a base (preferably, ammonia water) are fed to an oxime-forming reactor to liberate hydroxylamine in the reactor.

Since cyclododecanone oxime produced has a high melting point, the oxime-forming reaction requires a solvent. One of the requirements as a reaction solvent is higher solubility for dissolving cyclododecanone oxime. When a solubility parameter as defined by the following equation is used as an index, a solvent having the parameter of 7.5 to 13.0, particularly 8.0 to 12.5 exhibits high solubility for dissolving cyclododecanone oxime.

Here, a solubility parameter indicates strength of an intermolecular binding force such as hydrogen bond, and generally the higher parameter shows the higher polarity. Compounds having close solubility parameter values exhibit high compatibility. This parameter can be calculated from $\Delta H^V$, a standard boiling point and density data, and $\Delta H^V$ can be estimated from a molecular structure. Herein, some solvents were measured for a solubility of cyclododecanone oxime and compared it with a calculated solubility parameter to determine an index.

$$\delta = ((\Delta H^V - RT)/V)^{1/2}$$

wherein $\delta$: solubility parameter, $\Delta H^V$: evaporation enthalpy change, R: gas constant, T: absolute temperature, V: molar volume.

Solvents which are reactive with cyclododecanone and/or hydroxylamine must be excluded even if they are good solvent exhibiting high dissolving power to cyclododecanone oxime. For example, ketones or aldehydes cannot be used because they react with hydroxylamine to form ketoximes or aldoximes, respectively. Nitrile reacts with hydroxylamine to form amidoximes. Amides also react with hydroxylamine to form adducts with the hydroxylamine. Furthermore, amines react with cyclododecanone to form Schiff bases. These solvents are excluded, even if they exhibit high solubility for dissolving cyclododecanone oxime.

Usable solvents for oxime formation are those that exhibit high solubility for dissolving cyclododecanone oxime and are inert to cyclododecanone and/or hydroxylamine. However, highly hydrophobic solvents lead to a slow oxime-formation rate and thus a longer reaction time. On the other hand, highly hydrophilic solvents are soluble in an aqueous phase and thus must be recovered from both oil and aqueous phases, which is disadvantageous in the aspects of facilities and energy. For example, due to the above reason, disadvantageous are chain hydrocarbons such as n-hexane, n-octane, isooctane, n-decane and n-dodecane, water-soluble alcohols and ethers having 1 to 2 carbon atoms such as methanol, ethanol and ethyleneglycol.

Therefore, the oxime-formation solvent preferably includes, for example, alicyclic hydrocarbon, fused-aromatic-ring hydrogenated-product, aromatic hydrocarbon, middle and higher alcohols, ethers, glymes, esters and the like. As necessary, surfactant and the like may be added to these solvents to increase the rate of oxime-formation.

If those having modest hydrophilicity are selected, it is possible to use middle and higher alcohols, ethers, glymes (polyether obtained by condensing ethylene glycol), esters and the like without adding surfactant and the like.

As the middle and higher alcohols, preference is given to monoalcohols having 3 to 12 carbons and these alcohols are preferred due to their good balance between hydrophilicity and hydrophobicity. They include, for example, 1-propanol, 2-propanol, 1-butanol, 2-butanol, isobutyl alcohol, tertiary butyl alcohol, amyl alcohol, isoamyl alcohol, hexanol, pentanol, heptanol, octanol, decanol, dodecanol, cyclohexanol, cyclooctanol, cyclododecanol and the like.

As ethers, preference is given to those having a solubility parameter not lower than 7.5 and they include, for example, anisole, anethole, allyl ethyl ether, allyl phenyl ether, cresol methyl ether, methoxynaphthalene, ethoxynaphthalene and benzofuran.

As glymes (glycol diethers), preferable use is made on them except those having extremely high solubility with water and they include, for example, monoglyme, t-butyl glyme, butyl diglyme, triglyme and tetraglyme.

As esters, preference is given to carboxylate ester and it includes, for example, methyl acetate, ethyl acetate, propyl acetate, hexyl acetate, benzyl acetate, methyl propionate, ethyl propionate, methyl isovalerate, ethyl isovalerate, methyl isobutyrate, ethyl octanoate, diethyl succinate, dimethyl succinate, diethyl oxalate, diethyl glutarate, methyl benzoate, ethyl benzoate, diethyl phthalate and dibutyl phthalate.

Although alicyclic hydrocarbon, fused-aromatic-ring hydrogenated-product and aromatic hydrocarbon are nonpolar solvent, they are usable and surfactant may be added as necessary. Since aromatic hydrocarbon, fused-aromatic-ring hydrogenated-product, alicyclic hydrocarbon having a side chain(s) and the like are also usable as the rearrangement solvent described later, they are preferred in the respect of simplification of steps.

As the aromatic hydrocarbon, preference is given to benzene, toluene, xylene, ethylbenzene, propylbenzene, butylbenzene, trimethylbenzene, tetramethylbenzene and cyclohexylbenzene, and particular preference is given to benzene, toluene, xylene. As the fused-aromatic-ring hydrogenated-product, preference is given to tetralin, decalin and dihydronaphthalene, and particular preference is given to tetralin and decalin. In addition, as the alicyclic hydrocarbon, preference is given to alicyclic hydrocarbon having a side chain(s) and preference is given to isopropylcyclohexane, methylcyclohexane, dimethylcyclohexane and ethylcyclohexane, preference is given to isopropylcyclohexane.

In the oxime-formation solvent, the rearrangement solvent described later may be present and mixed with the oxime-formation solvent unless it reacts with cyclododecanone and/or hydroxylamine.

Although the oxime-forming reaction may be conducted at a high temperature, the reaction at a temperature of 100° C. or higher requires a pressurized vessel because hydroxylamine is used as an aqueous solution. The reaction is, therefore, preferably conducted at 100° C. or lower and under the ambient pressure. On the other hand, the reaction at a lower temperature leads to reduction in a reaction rate. A temperature is, therefore, preferably 60° C. or higher, more preferably 75° C. or higher.

The reaction time of the oxime-forming reaction varies depending on the oxime-formation solvent and its temperature. However, the time is 0.5 hours to 10 hours, preferably 1 hour to 6 hours in the case of conducting the reaction using the above-mentioned monoalcohol having 3 to 12 carbons as the solvent at 75° C. In the case of shorter reaction time, unreacted hydroxylamine and cyclododecanone would remain. Although the unreacted starting materials may be recycled to a step for producing the starting materials and the like, a recycling facility would be required, which is not preferred. In the case of longer reaction time, it is not preferred because equipment for the oxime-forming reaction would become longer and larger.

An oxime-forming reactor may be a common reactor such as batch reactor, semi-batch reactor, tubular reactor and tank flow reactor, and particularly continuous stirred tank flow reactor (CSTR) is suitable. When CSTR is used, an aqueous solution of hydroxylamine is fed to a first reactor and a cyclododecanone solution is fed to the final reactor, and it is desirable that an aqueous phase is transferred to the latter reactor and an oil phase is transferred to the former reactor sequentially so that reactants are completely reacted without remaining unreacted reactants.

In the subsequent oil/aqueous phase separation step, a reaction mixture after the oxime-forming step is separated into an oil phase and an aqueous phase to obtain the oil phase in which cyclododecanone oxime is dissolved. In the step, it is also preferred to add the rearrangement solvent (on the premise that it goes into oil phase) and carry out the oil/aqueous phase separation, which will be explained in detail for the dehydration/solvent preparation step. The oil phase and the aqueous phase can be separated by a commonly used separation method such as standing separation, centrifugation separation and cyclone separation, but in an industrial continuous process, a reaction mixture is transferred from an oxime-forming reactor to a separator, where the oil and the aqueous phases are separated and drained. Depending on the type of the oxime-forming reactor, the oil phase and the aqueous phase may be drained separately from the reactor. When oxime formation is conducted using an aqueous solution of hydroxylamine sulfate (hydroxylamine prepared by Rashig method, also called as ammonium sulfite method, where an aqueous solution of ammonium nitrate is reduced by sulfur dioxide in the presence of hydrogen sulfate ions, into hydroxyamide-N,N-disulfate, which is then hydrolyzed to obtain hydroxylamine sulfate) and ammonia water, ammonium sulfate is obtained as a byproduct from the separated aqueous phase. This ammonium sulfate is called as oxime ammonium sulfate, which is purified more easily than ammonium sulfate as a byproduct in the rearrangement step described in "BACKGROUND ART" (called as rearrangement ammonium sulfate) and can be thus sold in the market. When hydroxylamine prepared by HPO method wherein hydroxylamine phosphate is prepared is used, ammonium sulfate is not formed even in the oxime-forming step. Furthermore, for the purpose of recovering the oxime-formation solvent dissolved in the aqueous phase, the oxime-formation solvent and cyclododecanone oxime may be extracted with a hydrophobic solvent from the aqueous phase.

The subsequent dehydration/solvent preparation step is a step for removing a part or all of the oxime-formation solvent and dissolved water in the solution of cyclododecanone oxime which has been collected as an oil phase in the oil/aqueous phase separation step, and for converting the solvent in the cyclododecanone oxime solution into a solvent system suitable for the subsequent rearrangement reaction step. It is preferred to conduct the removal of the oxime-formation solvent by means of distillation, and it is also preferred to distill away and remove the dissolved water by this distillation at the same time. The oxime-formation solvent distillate is collected and recycled to the oxime-forming step, and used as the solvent of cyclododecanone solution to be supplied to the oxime-formation reaction. Water is also removed so that the concentration of water content in the cyclododecanone oxime solution to be transferred to the rearrangement step becomes 1,000 ppm or less, preferably 100 ppm or less.

When the oxime-formation solvent differs from the rearrangement solvent, the rearrangement solvent may be added after removing the oxime-formation solvent (for example, by means of distillation as described above) or before removing. In the case of adding the rearrangement solvent before removing the oxime-formation solvent, it is preferred that the rearrangement solvent has a boiling point higher than that of the oxime-formation solvent, and furthermore, when the rearrangement solvent is hydrophobic, preferably nonpolar solvent, it may be added to the oxime-formation solvent before the oil/aqueous phase separation. After the oil/aqueous phase separation, by means of distillation the oxime-formation solvent with lower boiling point is distilled and removed, and at the same time the dissolved water is removed by distillation. In this step, a portion of the rearrangement solvent may be distilled away. The solvent in the cyclododecanone oxime solution as the residue of this step is now substantively the rearrangement solvent, and the water concentration in the solution is adjusted to be 1,000 ppm or less, preferably 100 ppm or less as described in the foregoing. Then, the solvent as such is transferred to the rearrangement step.

When in this way, the rearrangement solvent is added prior to the oil/aqueous phase separation, the oil/aqueous phase separation step overlaps with the dehydration/solvent preparation step.

When the oxime-formation solvent is identical with the rearrangement solvent, it is preferred that while a portion of the oxime-formation solvent (i.e., the rearrangement solvent) is removed by distillation, the dissolved water is distilled away and removed at the same time. This step makes the water concentration of the solution to be 1,000 ppm or less, preferably 100 ppm or less. The water-containing solvent distillate is recycled to the oxime-forming step. In this case, the solvent per se is not replaced; yet the dissolved water is removed to prepare a substantially anhydrous solvent (The concentration of water content is preferably not more than 100 ppm.) suitable for the rearrangement reaction from the water-containing solvent.

When the oxime-formation solvent is identical with the rearrangement solvent, the solvent is preferably aromatic hydrocarbon, fused-aromatic-ring hydrogenated-product, or alicyclic hydrocarbon having side chain(s).

When, as described above, the dissolved water is removed by distillation, it is preferred to use two or more distillation columns as necessary. When, in particular, the oxime-formation solvent differs from the rearrangement solvent, after most of the oxime-formation solvent and water are distilled away in the first distillation column, residual liquid part is transferred into the second distillation column and the oxime-formation solvent and water, in particular water can be sufficiently removed while a portion of the rearrangement solvent is distilled away.

The dehydrated cyclododecanone oxime solution is transferred to the rearrangement step. In the rearrangement step, laurolactam is formed from cyclododecanone oxime by a rearrangement reaction using the aromatic-ring containing compound as a rearrangement catalyst.

An aromatic-ring containing compound used as a rearrangement catalyst is preferably an organic compound having a structure (1) containing at least one carbon atom having a leaving group as a ring member of the aromatic ring and (2) containing at least two carbon atoms having an electron-withdrawing group as ring members of the aromatic ring, and (3) wherein, three of the nitrogen atoms and/or the carbon atoms having an electron-withdrawing group, each of which is a ring member of the aromatic ring, are at the ortho and the para positions to the carbon atom having a leaving group described in (1).

Preferable examples of the aromatic ring include monocyclic or polycyclic aromatic rings such as benzene, biphenyl, terphenyl and triphenyl; fused polycyclic aromatic rings such as naphthalene, anthracene, fluorene, phenanthrene, azulene and pyrene; and aromatic heterocycles such as pyrrole, furan, thiophene, imidazole, pyrazole, triazole, tetrazole, oxazole, isoxazole, thiazole, isothiazole, furazanpyridine, pyrazine, pyrimidine, pyridazine and triazine; particularly preferably, benzene, pyridine, pyrimidine and triazine.

Examples of a leaving group may include halogen (fluorine, chlorine, bromine and iodine), sulfonyloxy {aryl sulfonyloxy such as benzenesulfonyloxy and p-toluenesulfonyloxy(tosyl) OTs; and alkanesulfonyloxy such as methanesulfonyloxy OMs, trifluoromethanesulfonyloxy(triflate) OTf, trichloromethanesulfonyloxy and ethanesulfonyloxy and the like}, sulfonyl halide (sulfonyl chloride, sulfonyl bromide and the like), diazonium, and carbonyl halide (carbonyl chloride). Particularly preferred is halogen, especially chlorine.

An electron-withdrawing group may be any known electron-withdrawing group without limitations and includes cyano, trifluoromethyl, trichloromethyl, nitro, halide (halogen), carbonyl and sulfonyl, preferably cyano and nitro.

Specific examples of a rearrangement catalyst may include benzene-ring compounds such as 4-chloro-3,5-dinitrobenzonitrile, 4-fluoro-3,5-dinitrobenzonitrile, 4-bromo-3,5-dinitrobenzonitrile, 4-chloro-1,3,5-trinitrobenzene, 4-trifluoromethyl-3,5-dinitrobenzonitrile, 4-p-toluene sulfonyloxy-3,5-dinitrobenzonitrile, picryl chloride, picryl bromide and picryl fluoride, and heterocyclic compounds such as 2-chloro-3,5-dinitropyridine, 2-bromo-3,5-dinitropyridine, 2-fluoro-3,5-dinitropyridine, trichlorotriazine, tribromotriazine and trifluorotriazine.

Particularly preferable examples include 4-chloro-3,5-dinitrobenzonitrile, picryl chloride, 2-chloro-3,5-dinitropyridine and trichlorotriazine, and particularly preferred is trichlorotriazine, which is highly active and inexpensive.

In addition, acids such as hydrogen chloride can be added as a co-catalyst to improve a rearrangement reaction rate. In particular, a Lewis acid is preferable because it can improve a rearrangement reaction rate without accelerating hydrolysis of cyclododecanone oxime. Examples of a Lewis acid generally include, but not limited to, zinc chloride, aluminum chloride, antimony pentachloride and tin tetrachloride, and preference is given to zinc chloride and tin tetrachloride, and particularly preferably zinc chloride which is significantly effective in improving a reaction rate.

The rearrangement reaction is carried out in the presence of the solvent. In descriptions above and below, the solvent to be used for the rearrangement reaction is referred to as the rearrangement solvent. In more detail, it is the solvent dissolving cyclododecanone oxime when the cyclododecanone oxime solution is transferred to the rearrangement step. The necessary requirements for the rearrangement solvent are (1) it has excellent solubility with cyclododecanone oxime and laurolactam; (2) it dissolves the rearrangement catalyst and does not react with the rearrangement catalyst; and (3) it is readily collected and recycled, and it has high stabilities thermally and chemically.

Using the aforementioned solubility parameter as an index in respect to the solubility with cyclododecanone oxime, the solvents with the solubility parameter of 7.5 to 13.0, in particular 8.0 to 12.5 are employed, in which, however, those reacting with elimination groups are excluded. In the case the elimination group is, for example, a halogen atom, water, alcohols, amines, mercaptans, amides and the like cannot be used.

Other solvents than the above excluded solvents may be used as the rearrangement reaction without problem. Generally a polar solvent is employed to dissolve the rearrangement catalyst or the rearrangement catalyst and a cocatalyst and to raise its acidity after dissolving them to increase the reaction rate of the rearrangement. In the aforementioned "Patent Reference No. 11," for example, nitriles are employed as a solvent. However, nitriles are not preferred because they are hydrolyzed to yield a corresponding amide when removing the catalyst, as described later.

Polar solvent are not preferred because they may react during the removal of catalyst and recovering of solvent due to their higher boiling point and higher reactivity in comparison with nonpolar solvents with the same number of carbon atoms, leading to a decrease in recovering ratio and degradation of quality of laurolactam.

Therefore, preference is given to nonpolar solvents as the rearrangement solvent. Nonpolar solvents facilitate the separation and removal of catalyst, and have no adverse effect on the quality of laurolactam. They are also preferred because they are recovered by distillation easily and have little loss in the recovery. Among nonpolar solvents, preference is given to aromatic hydrocarbon, fused-aromatic-ring hydrogenated-product and alicyclic hydrocarbon (in particular, alicyclic hydrocarbon having a side chain(s)). As the aromatic hydrocarbon, preference is given to benzene, toluene, xylene, ethylbenzene, propylbenzene, butylbenzene, trimethylbenzene, tetramethylbenzene and cyclohexylbenzene, and particular preference is given to benzene, toluene, xylene. As the fused-aromatic-ring hydrogenated-product, preference is given to tetralin, decalin and dihydronaphthalene, and particular preference is given to tetralin and decalin. In addition, as the alicyclic hydrocarbon having a side chain(s), preference is given to isopropylcyclohexane, methylcyclohexane, dimethylcyclohexane and ethylcyclohexane, and particular preference is given to isopropylcyclohexane.

The amount of the rearrangement catalyst varies depending on the water content in the cyclododecanone oxime, and is 0.01 mol % to 20 mol %, preferably 0.1 mol % to 5 mol % to cyclododecanone oxime. If the amount of the catalyst is too small, a rearrangement rate is so slow that the unreacted cyclododecanone oxime may unfavorably remain. In contrast, the excessive amount of the catalyst increases a catalyst cost, and unfavorably increases costs for post-treatment (i.e. removal) or recycling of the catalyst. The amount of the co-catalyst is 0.1 to 10 molar amount, preferably 0.5 to 5 molar amount to the catalyst. A too small amount of the co-catalyst is less effective in improving a rearrangement rate while an excessive amount of the co-catalyst cannot further improve a rearrangement rate.

A reaction temperature in the rearrangement step is 50° C. to 160° C., preferably 80° C. to 110° C. A too low reaction temperature is unfavorable because a reaction rate is reduced, leading to a longer reaction time. At a low temperature, cyclododecanone oxime is less soluble in the rearrangement solvent and the amount of the solvent to be recovered or recycled is increased. On the other hand, a too high reaction temperature is unfavorable because heat generated in the exothermic rearrangement reaction may cause rapid increase in a temperature to the extent that the reaction cannot be controlled. Furthermore, a too high reaction temperature unfavorably leads to decrease in a rearrangement yield and deterioration in product quality such as coloration problem.

A reaction time of the rearrangement step is 5 min to 10 hours, preferably 20 min to 4 hours. A reaction time varies depending on the type a catalyst, a catalyst concentration and a reaction temperature, but the above reaction conditions are adjusted such that the reaction can be easily controlled and a very large reactor volume is not required.

The reaction can be conducted under a reduced pressure, an ambient pressure or an increased pressure. Although it is not strongly recommended that the reaction is conducted under an increased pressure, the reaction can be conducted in a closed system, whereby a component eliminated from the catalyst (for example, when the leaving group is halogen, it is hydrogen halide) is prevented from diffusing to the outside of the reaction system. Employing a closed process is preferable because a facility for adsorbing or removing the compound originated from the leaving group can be reduced and the compound originated from the leaving group itself is an acid which can act as a co-catalyst accelerating the rearrangement reaction.

A rearrangement reactor may be a common reactor such as batch reactor, tubular reactor and tank flow reactor, and particularly continuous stirred tank flow reactor (CSTR) is suitable in the light of easy control of a reaction temperature and simple operation.

The subsequent separation/purification step is a step for separating and removing the rearrangement solvent and the rearrangement catalyst from the reaction mixture after the rearrangement step to obtain purified laurolactam.

First, there are a distillation method and a quench method of adding water or alkali, as the method for separating and removing the catalyst and cocatalyst from the reaction liquid. When the liberated catalyst and cocatalyst have a lower boiling point than that of laurolactam, they may collected by distillation under reduced pressure and recycled to the rearrangement step; however, preference is given to the quench removal after completion of the rearrangement because even a trace amount of the catalyst contaminating laurolactam would degrade its quality. In the case of the quench by adding water, the leaving group of the catalyst is replaced by hydroxyl group and the catalyst migrates into aqueous-phase side. For example, trichlorotriazine turns into cyanuric acid and dissolves in an aqueous-phase. Since the acids used for the cocatalyst are also soluble in water, they can be removed by washing with water. To facilitate the removal of the catalyst, use of an alkali aqueous solution such as aqueous ammonia and aqueous sodium hydroxide may be used.

Further purification of laurolactam typically involves distillation operations (including obtaining a product as a distillate, obtaining a product as a still-bottom product, rectification and so forth), which are preferably combined as a multistage procedure. Since the rearrangement solvent generally has a lower boiling temperature than laurolactam, the remained still residue (still-bottom product) after recovering the rearrangement solvent by distillation can be drained and distilled one or more times to be purified.

There are no particular restrictions to the distillation conditions and a distillation apparatus in the separation/purification step, but for preventing ring opening or polymerization of laurolactam, it is desirable that vacuum distillation is conducted at a vacuum of 10 torr or less such that a bottom temperature is 250° C. or lower, preferably 220° C. or lower.

As is clear from the above descriptions, each step in the production process of the present invention may be a combination of two or more substeps, or, if possible, two or more steps may be conducted in the same apparatus or carried out simultaneously. Although the present invention is preferably utilized in a continuous production process, for example, as in an industrial process, some or all steps may be independently conducted.

EXAMPLES

Figure 2:
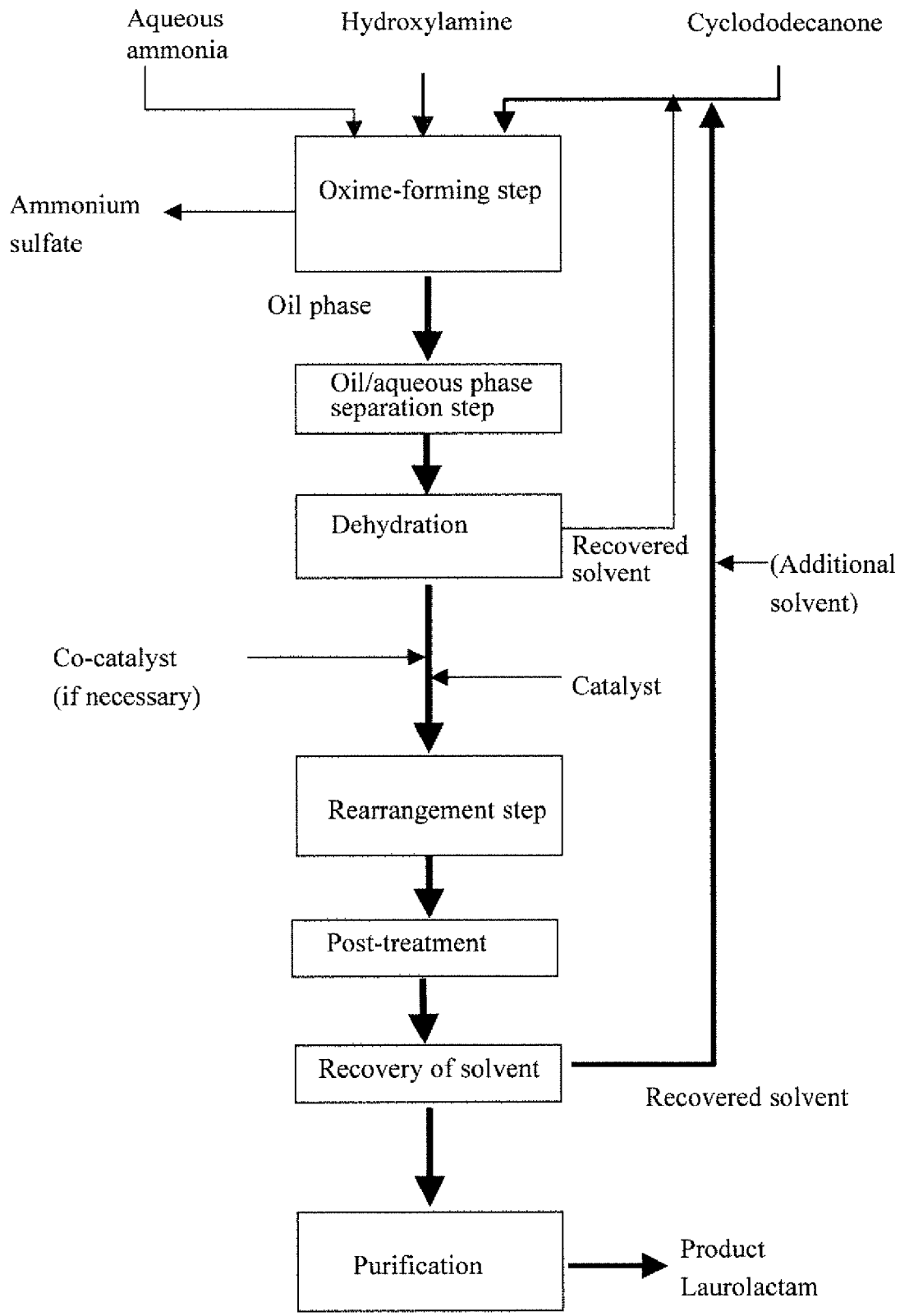
FIG. 2 is a flowchart showing the process flow of Example 5.

Then, the present invention will be specifically explained by illustrating examples. The present examples intend to show an example of embodiments of the present invention, and the present invention is not limited by the present examples. In addition, the process flows of Examples 1 to 4, i.e., in the case that the oxime-formation solvent differs from the rearrangement solvent, are shown in FIG. 1, and the process flow of Example 5, i.e., in the case that the oxime-formation solvent is identical with the rearrangement solvent, is shown in FIG. 2.

Example 1

Oxime-Forming and Oil/Aqueous Phase Separation Steps

Into a pillow type first reactor for oxime-formation with a 30 L liquid phase zone which was internally divided into four chambers each of which was equipped with an agitating blade were fed a 15% by weight aqueous solution of hydroxylamine sulfate (Wako Pure Chemical Industries, Ltd.) at 3 kg/h and the oil phase from a second reactor for oxime-formation. The reaction temperature was set at 80° C. and 25% by weight of aqueous ammonia was fed into each chamber at 63 g/h to carry out the oxime formation reaction. The reaction mixture was separated into phases of liquid after toluene was added at 1 kg/h, and the oil phase composed of cyclododecanone, 2-propanol and toluene was transferred to the dehydration/solvent preparation step while the aqueous phase was fed into the second rector for oxime formation. The second rector for oxime formation was a 15 L pillow type rector which was internally divided into four chambers, and to the second reactor were fed the above aqueous phase of the oxime-formation reaction mixture and 25% by weight of cyclododecanone in 2-propanol solution at 4 kg/h (equimolar amount to hydroxylamine sulfate fed to the first reactor), the reaction temperature was set at 80° C. and 25% by weight of aqueous ammonia was fed into each chamber at 31 g/h to carry out the oxime formation reaction. The obtained reaction mixture was separated into phases of liquid, and the oil phase was fed into the first reactor for oxime formation. To the aqueous phase, toluene was added at 650 g/h and 2-propanol and cyclododecanone oxime dissolved in water were collected by a counter flow extraction, and they were transferred to the dehydration/solvent preparation step.

The aqueous phase, from which 2-propanol and cyclododecanone oxime were collected, was concentrated and after the precipitated ammonium sulfate was collected, it was disposed of as waste water.

(Dehydration/Solvent Preparation Step)

This step is composed of two distillation equipments. Cyclododecanone oxime obtained in the oil/aqueous phase separation step was transferred into the first distillation equipment, and 2-propanol and dissolved water were distilled away. Distillate was recycled to the oxime-forming step as the solvent of cyclododecanone. The residual liquid (still residue) in the first distillation equipment was transferred into the second distillation equipment, and a small amount of toluene containing water and 2-propanol was distilled out from the top of column and was recycled to the first distillation equipment. As a result of analyzing the residual liquid by means of gas chromatography, 2-propanol was not detected. As a result of measuring the concentration of water by Karl Fischer method, it was also found to be 50 ppm. The residual liquid was fed to the rearrangement step.

(Rearrangement Step)

Into a pillow type reactor with a 10 L liquid phase zone which was internally divided into three chambers each of which was equipped with an agitating blade were fed the toluene solution of cyclododecanone oxime obtained in the previous step and 3% by weight solution of trichlorotriazine in toluene were fed at 2,700 g/h and 1,000 g/h, respectively, and the rearrangement reaction was carried out at 90° C. (average residence time: 1.9 hours). As a result of collecting a portion of outflow fluid and analyzing it by means of gas chromatography, the yield amount of laurolactam was found to be 1,039 g/h and the yield of laurolactam on the basis of cyclododecanone was found to be 96.2%.

(Catalyst Removal Step)

The reaction mixture obtained in the rearrangement step was introduced to a stirred-tank-type washing tank, and washed with the water that was added in an amount of 0.2 times (ratio by weight) of the rearrangement liquid and separated into phases, further washed with 10% by weight of aqueous sodium hydroxide that was added in an amount of 0.5 times (ratio by weight) and the oil/aqueous phase separation was carried out.

(Cyclododecanone Collection and Laurolactam Purification Steps)

The separated oil phase was introduced to a continuous vacuum distillation equipment, and water, light by-products and toluene of solvent were first removed. Residue in the tank was introduced to the second distillation equipment, and laurolactam was distilled out. Residue in the tank was led to the third distillation equipment and distillate consisting of laurolactam was recycled to the second distillation equipment, and a part of the residue in the tank was cut off and its major part was recycled to the catalyst removal step. A continuous operation was conducted for 8 hours to obtain laurolactam with purity of 99.5%. Its yield against consumed cyclododecanone was 94.5% by mole.

Example 2

The reaction was carried out in a similar manner to Example 1 except that the feeding rate of 3% by weight solution of trichlorotriazine in toluene at the rearrangement step was changed to 330 g/h, and additionally 10% by weight of zinc chloride in toluene/laurolactam solution (the ratio of toluene/laurolactam is 111 (weight/weight)) was fed at 75 g/h. The yield of laurolactam until the rearrangement step was 97.5%, yield of laurolactam after distillation was 96.0% and its purity was 99.98%.

Example 3

After the oxime-formation reaction was carried out in a similar manner to Example 1 except that the feeding rates of cyclododecanone/(2-propanol, toluene) solution, hydroxylamine aqueous solution and aqueous ammonia at the oxime-forming step was doubled and the reaction temperature was 95° C., the dehydration and solvent replacement were carried out. While unreacted cyclododecanone was not detected in the residual liquid after the solvent replacement, 90 ppm of water and 50 ppm of 2-propanol were detected.

The reaction was carried out in a similar manner to Example 2 except that the feeding rates of the obtained cyclododecanone oxime solution, trichlorotriazine solution and the zinc chloride solution was doubled and the reaction temperature was 100° C. After washing with water and aqueous sodium hydroxide each in an amount of twice of Example 2, distillation and purification were carried out. The yield of laurolactam until the rearrangement step was 97.0%, yield of laurolactam after distillation was 95.8% and its purity was 99.85%.

Example 4

The reaction was carried out in a similar manner to Example 2 except that toluene in the Example 2 was replaced with isopropylcyclohexane and 2-propanol was replaced with 2-methyl-2-propanol. While unreacted cyclododecanone was not detected in the residual liquid after the solvent replacement, 90 ppm of water and 40 ppm of 2-methyl-2-propanol were detected. The yield of laurolactam after the rearrangement reaction was 96.5%, yield of laurolactam after distillation was 95.0% and its purity was 99.8%.

Example 5

The oxime-formation was carried out not using alcohol as the oxime-formation solvent but with toluene as the solvent. The feeding rates of the toluene solution of cyclododecanone, the aqueous solution of hydroxylamine sulfate and aqueous ammonia were all half amount of Example 2, and the reaction temperature was 95° C. After the completion of the reaction, the dissolved water in the solution was removed by extracting toluene at a distillation rate of about 650 g/h. The concentration of water after the dehydration was 50 ppm, and the residual ratio of cyclododecanone was 1.0% by mole. The feeding rates to a rearrangement reaction tank of the cyclododecanone oxime solution, trichlorotriazine solution and zinc chloride solution were all half amount of Example 2, and the rearrangement reaction was carried out and washing with water and washing with aqueous sodium hydroxide were carried out. The yield of laurolactam after the rearrangement reaction was 95.1%, yield of laurolactam after distillation was 94.0% and its purity was 99.3%.

Comparative Example 1

The reaction was carried out in a similar manner to Example 1 except that the rearrangement solvent was replaced with benzonitrile. As the passage of operation time benzamidoxime was detected which was generated by reaction of benzonitrile contained in the recycled liquid to the oxime-forming step with hydroxylamine. As this progress, an amount of cyclododecanone increased due to a shortage of hydroxylamine to be used for the oxime-formation reaction. Although the yield of laurolactam until the rearrangement step was initially 96.0%, the yield declined to 82% as a result of the operation after 8 hours. In addition, benzonitrile was hydrolyzed to yield benzamide and the like during the treatment with sodium hydroxide, and the purity of laurolactam obtained by distillation was 85%.

Comparative Example 2

The reaction was carried out in a similar manner to Example 2 except that the rearrangement solvent and the solvent dissolving trichlorotriazine and zinc chloride were 1-methyl-2-pyrrolidone. As a result of collecting the rearrangement reaction mixture and carrying out gas chromatographic analysis, the yield of laurolactam was 27.2% and 70% of cyclododecanone oxime remained. Even though the feeding rates of the solution of cyclododecanone oxime and the solution of trichlorotriazine and zinc chloride were reduced half, and their residence time was prolong by twice, the conversion ratio of cyclododecanone oxime was not improved.

Comparative Example 3

The reaction was carried out in a similar manner to Example 1 except that merely one column of distillation for the dehydration/solvent preparation step was employed. In the cyclododecanone solution to be transferred to the rearrangement step, 1,500 ppm of water existed and hydrolysis of cyclododecanone oxime occurred during the rearrangement step to yield cyclododecanone. The yields until the rearrangement step were 90% for laurolactam and 6% for cyclododecanone.

INDUSTRIAL APPLICABILITY

An industrially advantageous and simple process for laurolactam is provided.

What is claimed is:

1. A process for producing laurolactam, comprising the steps of:
    (a) reacting cyclododecanone with hydroxylamine in an aqueous solution in the presence of an organic solvent ("oxime-formation solvent") to produce cyclododecanone oxime ("oxime-forming step");
    (b) separating the reaction mixture obtained after the oxime-forming step into an oil and an aqueous phase and collecting a solution of cyclododecanone oxime of the oil phase ("oil/aqueous phase separation step");
    (c) removing a part or all of the oxime-formation solvent and dissolved water from the solution of cyclododecanone oxime which is collected as an oil phase in the oil/aqueous phase separation step, thereby preparing a solution containing a solvent to be used in a rearrangement reaction in a later step ("rearrangement solvent") for the cyclododecanone oxime ("dehydration/solvent preparation step");
    (d) producing laurolactam from cyclododecanone oxime by a rearrangement reaction using an aromatic-ring containing compound selected from the group consisting of 4-chloro-3,5-dinitrobenzonitrile, picryl chloride, 2-chloro-3,5-dinitropyridine and trichlorotriazine as a rearrangement catalyst ("rearrangement step");
    (e) separating and removing the rearrangement solvent and the rearrangement catalyst from the reaction mixture obtained after the rearrangement step; and purifying the laurolactam ("separation/purification step").

2. The process for producing laurolactam according claim 1, wherein in the dehydration/solvent preparation step, a content of residual water in the cyclododecanone oxime solution to be fed to the rearrangement step is reduced to 1000 ppm or less.

3. The process for producing laurolactam according to claim 2, wherein in the dehydration/solvent preparation step, a content of residual water in the cyclododecanone oxime solution to be fed to the rearrangement step is reduced to 100 ppm or less.

4. The process for producing laurolactam according to claim 1, wherein the rearrangement solvent is a nonpolar solvent.

5. The process for producing laurolactam according to claim 4, wherein the rearrangement solvent is one or more solvents selected from the group consisting of alicyclic hydrocarbon, aromatic hydrocarbon and fused-aromatic-ring hydrogenated-product.

6. The process for producing laurolactam according to claim 4, wherein prior to the oil/aqueous phase separation step, the rearrangement solvent is added and the oxime-formation solvent is removed by distillation in the dehydration/solvent preparation step.

7. The process for producing laurolactam according to claim 4, wherein the oxime-formation solvent and the rearrangement solvent are an identical organic solvent, and a portion thereof is removed by distillation in the dehydration/solvent preparation step.

* * * * *